(12) United States Patent
Ejima et al.

(10) Patent No.: US 7,501,495 B2
(45) Date of Patent: Mar. 10, 2009

(54) METHOD FOR IMPROVING RECOVERY YIELD IN PROTEIN PURIFICATION WITH GEL FILTRATION CHROMATOGRAPHY

(75) Inventors: Daisuke Ejima, Kawasaki (JP); Ryosuke Yumioka, Kawasaki (JP); Tsutomu Arakawa, Thousand Oaks, CA (US)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/276,509

(22) Filed: Mar. 3, 2006

(65) Prior Publication Data

US 2006/0199948 A1 Sep. 7, 2006

Related U.S. Application Data

(60) Provisional application No. 60/657,735, filed on Mar. 3, 2005.

(51) Int. Cl.
*C12P 21/08* (2006.01)
*C07K 1/10* (2006.01)
*C07K 1/16* (2006.01)
*C07K 16/00* (2006.01)

(52) U.S. Cl. .................. 530/387.1; 530/412; 530/417
(58) Field of Classification Search .............. 424/130.1; 514/3
See application file for complete search history.

(56) References Cited

U.S. PATENT DOCUMENTS 6,489,292 B1 * 12/2002 Havelund et al. ............... 514/3
2004/0197324 A1 * 10/2004 Liu et al. ................. 424/130.1
2005/0176109 A1    8/2005 Yumioka et al.

OTHER PUBLICATIONS

Birch, J. R., et al., "The Production of Monoclonal Antibodies," Monoclonal Antibodies: Principles and Applications, pp. 231-265, 1995 Wiley-Liss, Inc.

Bleeker, W. K., et al., "Vasoactive side effects of intravenous immunoglobulin preparations in a rat model and their treatment with recombinant platelet-activating factor acetylhydrolase," Blood 2000;95(5):1856-1861.
Edited by Franks, F., "Protein Biotechnology—Isolation, Characterization and Stabilization," Copyright 1996 by Baifukan Co., Ltd., pp. 64-67, with English translation of p. 66, line 6 and Table 3-5.
Ejima, D., et al., "Arginine as an effective additive in gel permeation chromatography," J. Chromatography 2005;1094:49-55.
Hartmann, W. K., et al., "Characterization and analysis of thermal denaturation of antibodies by size exclusion high-performance liquid chromatography with quadruple detection," Analytical Biochem. 2004;325:227-239.
Paborji, M., et al., "Chemical and Physical Stability of Chimeric L6, a Mouse-Human Monoclonal Antibody," Pharm. Res. 1994;11(5):764-771.
Štulík, K., et al., "Some potentialities and drawbacks of comtemporary size-exclusion chromatography," J. Biochem. Biophys. Methods 2003;56:1-13.
Ishibashi, M., et al., "Is arginine a protein-denaturant?" Protein Exp. Purif. 2005;42:1-6.
Tsumoto, K., et al., "Role of Arginine in Protein Refolding, Solubilization, and Purification," Biotechnol. Prog. 2004;20:1301-1308.
Umetsu, M., et al., "Nondenaturing solubilization of β2 microglobulin from inclusion bodies by L-arginine," Biochem. Biophys. Res. Comm. 2005;328:189-197.
Search Report for EP Patent App. No. 06003720.7 (Jun. 21, 2006).
U.S. Appl. No. 60/537,503, Ryosuke et al., filed Jan. 21, 2004.
U.S. Appl. No. 60/631,407, Yumioka et al., filed Nov. 30, 2004.

* cited by examiner

*Primary Examiner*—Jon P Weber
*Assistant Examiner*—Marsha M Tsay
(74) *Attorney, Agent, or Firm*—Shelly Guest Cermak; Cermak Kenealy Vaidya & Nakajima LLP.

(57) ABSTRACT

A method to more quantitatively recover a peak of a protein and associated aggregates, hydrophobic proteins, or hydrophobic peptides which are typically difficult to recover and detect as a peak, using a commercially available gel filtration chromatography column and a mobile phase is described. More specifically, a compound, such as arginine, which may be added to the mobile phase, thereby eliminating the unnecessary interaction that occurs between the proteins, peptides, or aggregates and the column stationary phase, is described.

3 Claims, 5 Drawing Sheets

METHOD FOR IMPROVING RECOVERY YIELD IN PROTEIN PURIFICATION WITH GEL FILTRATION CHROMATOGRAPHY

This application claims priority under 35 U.S.C § 119(e) to U.S. provisional application 60/657,735, filed on Mar. 3, 2005, the entirety of which is incorporated by reference.

BACKGROUND OF THE INVENTION

1. Field of the Invention

The present invention relates to a method for improving the yield of a protein that is typically difficult to purify using gel filtration chromatography and a water soluble buffer. More specifically, the invention relates to a protein purification method whereby the addition of arginine to a developing solvent enables improvement in recovery yields of antibodies, hydrophobic proteins, or hydrophobic peptides.

2. Brief Description of the Related Art

Knowledge of the molecular weight distribution of a protein in a solution is an extremely important factor in defining a molecular association unit required for expressing the function of the protein. Furthermore, extremely significant problems are encountered when proteins associate or aggregate, often changing their natural state, such as changing their function, or exerting a distinct action different from the expected action (i.e., adverse effect), or loss of stability. For example, monoclonal antibodies intended for use in therapy may exert proper action and stability as long as they are present as a monomer; however, it has been observed that when aggregates form, serious adverse effects may occur, including antigenicity changes and/or deterioration of storage stability (Pharmaceutical Research, 11 (1994), 764-771; Blood, 95 (2000), 1856-1861).

Examination of molecular weight distribution of a protein is regarded as an important technique not only for basic biochemistry research, but also for research and development and quality control of proteinous pharmaceutical products. Known methods for determining molecular weight distribution of a protein include gel filtration chromatography, ultracentrifugal analysis, electrophoretic analysis, light scattering analysis, dynamic light scattering analysis, and the like. Recently, X-ray small angle scattering has also been utilized, and is recognized as a practical technique. However, among these techniques, gel filtration chromatography is most frequently chosen over the other techniques in proteins production laboratories for determining the molecular weight distribution in an aqueous solution. Gel filtration chromatography is considered to be capable of providing information comparable to ultracentrifugal analysis since it employs not only ultraviolet absorption but also light scattering, refractive index, and density in combination (Analytical Biochemistry, 325 (2004), 227-239).

However, gel filtration chromatography continues to present some problems. The elution order of proteins depends on their molecular weight due to diffusion in voids of the stationary phase on the column. The elution order, measured by retention time, is converted into molecular weight. However, the protein not only distributes in the voids of the stationary phase, but also interacts with the stationary phase itself. When the interaction is potent, the elution order may be retarded and may possibly affect the molecular weight information. Because interaction of the aggregates of the protein with the filler is particularly strong, elution from the column in a peak may also be completely inhibited. In such instances, despite of inclusion of the aggregates, an erroneous conclusion that no aggregates are included may be reached by the analysis of the gel filtration chromatography results. It is generally understood that gel filtration chromatography of not just aggregates, but also highly hydrophobic proteins or peptides is difficult. In view of this, it was proposed to optimize the combination of the stationary phase, the mobile phase (developing solvent) and detection method during gel filtration chromatography [Journal of Biochemical and Biophysical Methods, 56 (2003), 1-13]. However, a procedure which alleviates the interaction between protein aggregates, highly hydrophobic proteins, or a highly hydrophobic peptides, and a column stationary phase, so to perfect the recovery in a peak has not been found. As reported by Stulik et al. [Journal of Biochemical and Biophysical Methods, 56 (2003), 1-13], even when an appropriate amount of an additive which is expected to alleviate the interaction between a column stationary phase and a protein, such as for example, an acid, an inorganic salt, or an organic solvent, is added to the mobile phase, improvement of the separation of the aggregates is only occasionally achieved. Furthermore, addition of an appropriate amount of a protein denaturating agent, which is expected to efficaciously alleviate the interaction, into the mobile phase has also been reported; however, difficulty in determining the conditions due to the risk of simultaneous protein degeneration is often encountered. Accordingly, when performing gel filtration chromatography of a protein which may include aggregates, a highly hydrophobic protein, or a highly hydrophobic peptide, it is strongly desirable to be able to easily determine conditions for quantitatively recovering a the aggregates or the hydrophobic protein peak.

SUMMARY OF THE INVENTION

An object of the present invention is to more quantitatively recover a peak of a protein aggregates, hydrophobic proteins or hydrophobic peptides, which are typically difficult to recover and detect as a peak, using a commercially available gel filtration chromatography column and a mobile phase. More specifically, it is an object of the present invention to find a compound which may be added to the mobile phase, and which has not been typically used in a mobile phase.

It is further object of the present invention to provide a method for improving the yield of a product selected from the group consisting of an antibody, a hydrophobic protein, and a hycrophobic peptide when performing gel filtration chromatography of a solution containing said product, comprising adding 0.05M to 1.5M arginine and/or an arginine derivative to a developing solvent utilized during said chromatography, wherein said antibody may be present as an aggregate.

It is a further object of the present invention to provide the method as described above, wherein the concentration of the arginine and/or arginine derivative in the developing solvent is 0.05M to 1.25M.

It is a further object of the present invention to provide the method as described above, wherein the concentration of the arginine and/or arginine derivative in the developing solvent is 0.10M to 0.75M.

BRIEF DESCRIPTION OF THE DRAWINGS

FIG. 1-2: Gel filtration chromatography of mouse monoclonal antibody (0.2 M arginine hydrochloride added to the developing solvent), wherein the large arrowhead indicates the monomer, and the small arrowhead indicates the aggregates. Details of the conditions are set forth in the detailed description.

FIG. 2-1: Gel filtration chromatography of human activin (0.75 M sodium chloride added to the developing solvent), wherein the large arrowhead indicates human activin. The solvent included in the sample gave a peak which overlapped with the part indicated by the arrowhead. Details of the conditions are set forth in the detailed description.

FIG. 2-2: Gel filtration chromatography of human activin (0.75 M arginine hydrochloride added to the developing solvent), wherein the large arrowhead indicates the monomer, and the small arrowhead indicates the aggregates. Peaks after 20 min represent the solvent included in the sample. Details of the conditions are set forth in the detailed description.

FIG. 3-1: Gel filtration chromatography of human interleukin 6 (0.75 M sodium chloride added to the developing solvent), wherein the large arrowhead indicates the monomer, and the small arrowhead indicates the aggregates. Peaks after 20 min represent the solvent included in the sample. Details of the conditions are set forth in the detailed description.

FIG. 3-2: Gel filtration chromatography of human interleukin 6 (0.75 M arginine hydrochloride added to the developing solvent), wherein the large arrowhead indicates the monomer, and the small arrowhead indicates the aggregates. Peaks after 20 min represent the solvent included in the sample. Details of the conditions are set forth in the detailed description.

FIG. 4-1: Gel filtration chromatography of human fibroblast growth factor (0.2 M sodium chloride added to the developing solvent), wherein the arrowhead indicates the human fibroblast growth factor. The large peak found thereafter represents the solvent included in the sample. Details of the condition are set forth in the detailed description.

FIG. 4-2: Gel filtration chromatography of human fibroblast growth factor (0.2 M arginine hydrochloride added to the developing solvent), wherein arrowhead indicates the human fibroblast growth factor. The large peak found thereafter represents the solvent included in the sample. Details of the conditions are set forth in the detailed description.

FIG. 5-1: Gel filtration chromatography of human interferon gamma (0.4 M sodium chloride added to the developing solvent), wherein the details of the conditions are set forth in the detailed description.

FIG. 5-2: Gel filtration chromatography of human interferon gamma (0.4 M arginine hydrochloride added to the developing solvent), wherein the arrowhead indicates the human interferon gamma. Peaks after 20 min represent the solvent included in the sample. Details of the conditions are set forth in the detailed description.

DETAILED DESCRIPTION OF EXEMPLARY EMBODIMENTS

Figure 1:
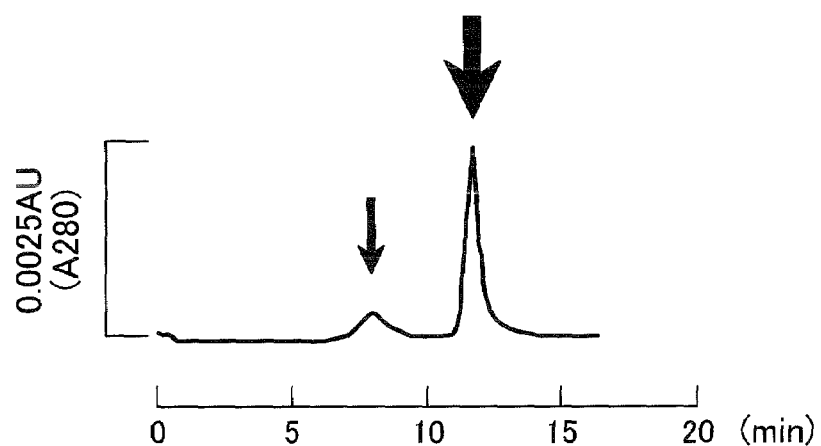
FIG. 1-1: Gel filtration chromatography of mouse monoclonal antibody (0.2 M sodium chloride added to the developing solvent), wherein the large arrowhead indicates the monomer, and the small arrowhead indicates the aggregates. Details of the conditions are set forth in the detailed description.

Accordingly, an aspect of the present invention is to provide a method for more quantitatively recovering aggregates, hydrophobic proteins or hydrophobic peptides when performing gel filtration chromatography of proteins which include aggregates, hydrophobic proteins, or hydrophobic peptides, through adding an appropriate amount of arginine into a water soluble buffer of the developing solvent, thereby eliminating the unnecessary interactions that often occur between proteins and the column stationary phase.

Interaction between the column stationary phase and proteins, which was recognized as a significant problem, can be alleviated by adding arginine into a water soluble buffer of the developing solvent. It is known that arginine does not affect the stability or structure of a protein. Therefore, according to the present invention, improved recovery of peaks in gel filtration chromatography of protein aggregates, hydrophobic proteins, or hydrophobic peptides can be obtained without affecting the structure or stability of the proteins. Therefore, the invention is applicable to not only analyses of proteins or peptides, but also methods for producing proteins employing gel filtration chromatography.

The arginine which may be used in the present invention may be the natural amino acid arginine and/or an arginine derivative. Examples of the arginine derivative include, in addition to arginine, acylated arginine such as acetyl arginine and N-butyloyl arginine, arginine butyl esters with the carboxyl group modified, agmatine with the carboxyl group eliminated, arginine having a hydroxyl group in place of an α-amino group, and the like. These may be used in the form of an acid addition salt. Examples of the acid which can form an acid addition salt include hydrochloric acid and the like.

Furthermore, the buffer into which the arginine and/or the arginine derivative is added may be adjusted so that the pH and buffer concentration is consistent with the properties of the target protein aggregates, hydrophobic proteins, or hydrophobic peptides, but any particular pH or buffer concentration is not required. Adjusting the pH may generally be carried out using the buffer for example, the sodium phosphate buffer, with no need to adjust the pH for the arginine and/or the arginine derivative. The arginine and/or the arginine derivative may be added to the buffer to give a concentration of 0.05 to 1.50 M, preferably 0.05 to 1.25 M, and more preferably 0.10 to 0.75 M. In this way, the recovery yield of the protein peak can be improved. The arginine and/or the arginine derivative may or may not be added into the solute, i.e., the solution containing an antibody including aggregates, hydrophobic proteins, or hydrophobic peptides. When it is desired to enhance the ionic strength of the solution, including the solute, the arginine and/or the arginine derivative may be added similarly.

Next, an isocratic elution method is preferred in the present invention Such methods are generally referred to as those in which one kind of buffer is used as the developing solvent.

Moreover, the gel filtration chromatography column used in the invention may be a commercially available product, and examples thereof include, for example, Superdex 200HR 10/30, Superdex 75HR 10/30 (both manufactured by Amersham Bioscience K.K.), TSK G3000SWXL (manufactured by Tosoh Corporation), and the like.

Examples of the protein which may be recovered in the invention include natural human antibodies, humanized antibodies, human-type antibodies prepared by recombinant DNA techniques, and monoclonal antibodies of mouse, and the like, including aggregates. Irrespective of species and subclass of the antibody, any one is applicable as long as it is an antibody which includes aggregates.

It is known that an antibody forms so-called aggregates through association with other molecules during the production step (concentration, exposure to acidic pH, heating manipulation) or storage step (solution, frozen solution, freeze-drying), which leads to deterioration of the activity and exertion of the adverse effect [Monoclonal Antibodies, Principles and Applications, p. 231-265, London: Wiley Liss, Inc., 1995]. Quantitative determination, and separation and removal of the aggregates are extremely important in industrial applications. Although the mechanism of formation of the aggregate is not uniform, it can not be readily dissociated into the monomer once formed. It is known that the aggregate exhibits greater hydrophobicity than the monomer, leading to a lower recovery yield during chromatography.

Furthermore, the invention is also applicable to proteins other than antibodies, such as proteins or peptides having high hydrophobicity, and/or those which are difficult to recover in a peak solely with use of a water soluble buffer. The invention is applicable to any method despite of the method of preparation, for example, extraction from nature, preparation with recombinant DNA techniques, or the like.

No consistent art-accepted definition has been adopted which distinguishes proteins from peptides. Although amino acid sequences having at least 50 amino acids may be considered to be a protein, this standard is not generally adopted. According to the invention, soluble compounds which are generally considered to be a peptide or a protein are intended.

Also, the hydrophobic protein and the hydrophobic peptide cannot be clearly defined, in general; however, proteins and peptides having a high content of hydrophobic amino acids are encompassed. When the proportion of hydrophobic amino acids is high, greater interaction of such a protein/peptide with the chromatography column stationary phase results, resulting in prolonged elution times. [Protein Biotechnology, pp. 67, BAIFUKAN CO., LTD, 1996]. The present invention describes methods for ameliorating the lower recovery yield which results from this hydrophobic interaction during chromatography.

When an antibody containing 60% aggregates is analyzed by gel filtration chromatography, the use of phosphate buffer solely in the developing solvent often results in a recovery yield of the antibody peak of less than 20% of the amount of the antibody loaded onto the column, even though all of the detected peaks are added together. Furthermore, in this instance, the content of the aggregates is often erroneously construed as being approximately 20%, and this is below the proper value of 60% by a large margin. However, when a phosphate buffer containing 0.2 M arginine is used as the developing solvent, the recovered antibody peak reaches almost 100% of the amount of the antibody loaded onto the column without altering any other condition. This result indicates the correct value of 60% for the aggregate content. The invention will be specifically explained with reference to following non-limiting Examples.

EXAMPLE 1

30 µl of 0.5 M sodium citrate (pH 2.72 adjusted to pH 3.04) was added to 120 µl of a 5.28 mg/ml purified anti-von Willebrand factor monoclonal antibody (mouse monoclonal antibody, subclass: $IgG_1$; WO96/17078) dissolved in an isotonic sodium phosphate buffer. 60 µl of 0.2 M citric acid (pH 4.50) and 240 µl of 3 M arginine hydrochloride (pH 4.52) were added to the above solution to further adjust the pH to 4.5. This solution was heated to 45° C. for 20 min. Then, 67.5 µl of 1 M Tris hydrochloride (pH 8.50) was added to adjust the volume to 517.5 µl and the pH to 5.13, followed by a final heating to 45° C. for 10 min. Immediately following this final heating, the mixture was cooled to room temperature, and the concentration of the antibody which remained in the supernatant was measured using a spectrophotometer. The antibody concentration was calculated based on the absorbance of 1.4 at a wavelength of 280 nm being 1 mg/ml. This mouse monoclonal antibody sample in a volume of 15 µl was subjected to gel filtration chromatography on a TSK G3000SWXL column using 0.1 M sodium phosphate (pH 6.8) as the developing solvent at a flow rate of 0.8 ml/min. Elution performance of the peak was studied using the ultraviolet absorption at a wavelength of 280 nm as a marker.

As shown in FIG. 1-1, the main component peak was found at a position that agrees with the elution position of the antibody monomer, while the aggregates were found as a subcomponent peak. 5.28 µg of a mouse monoclonal antibody which does not include the associated form was previously subjected to gel filtration chromatography under the same conditions as above, and the peak area per unit weight was determined from the area of the antibody peak detected at a wavelength of 280 nm. Using this value, the amount of the antibody recovered in a peak was calculated. The results are presented in Table 1. Measurement of the absorbance revealed that the amount of antibody remaining in the supernatant after heating was 92.4% of that before the heating. However, it was elucidated that total yield of the peaks of the recovered antibody monomer and aggregates as detected by gel filtration chromatography was low, or about 18.5% of that before the heating, suggesting possibly only ⅕ (fifth) of the antibody remained in the supernatant. The content of the aggregates occupying the entire peak then was 21.7%.

Figures 1, 2:
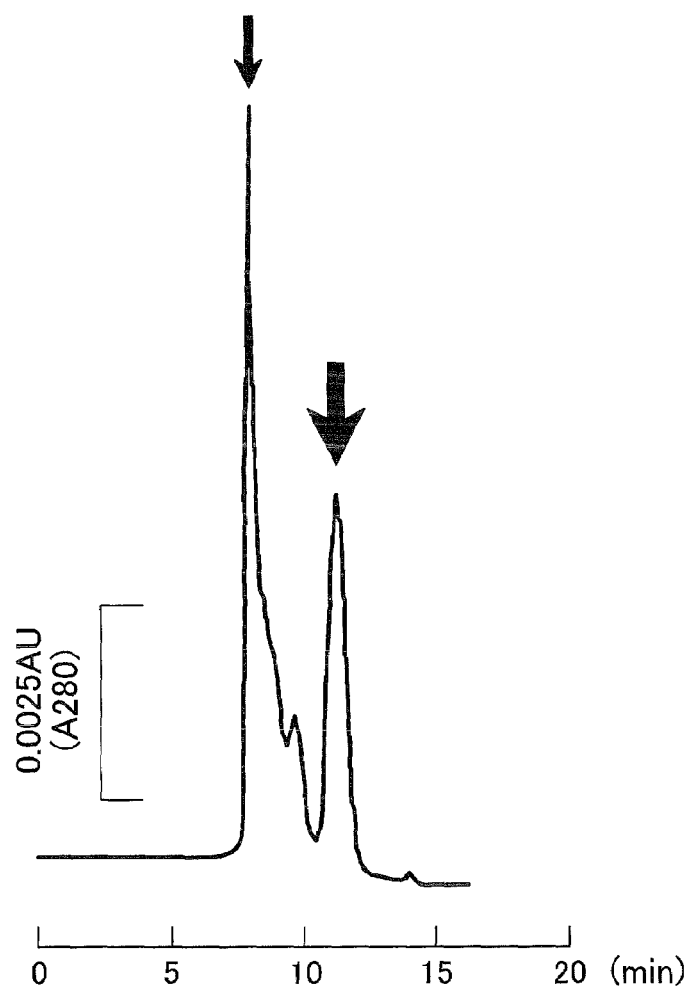
Figures 1, 2:
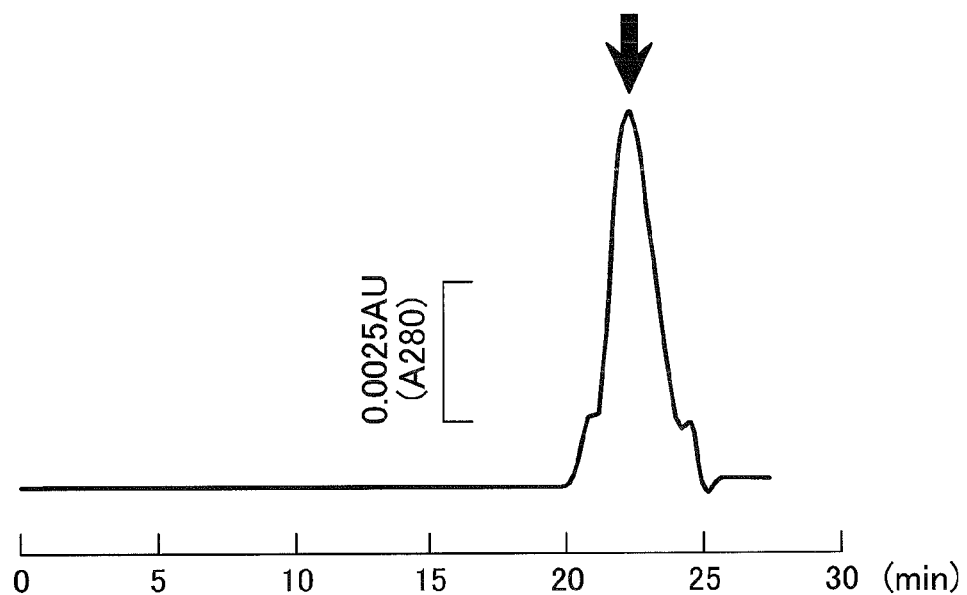
Figure 2:
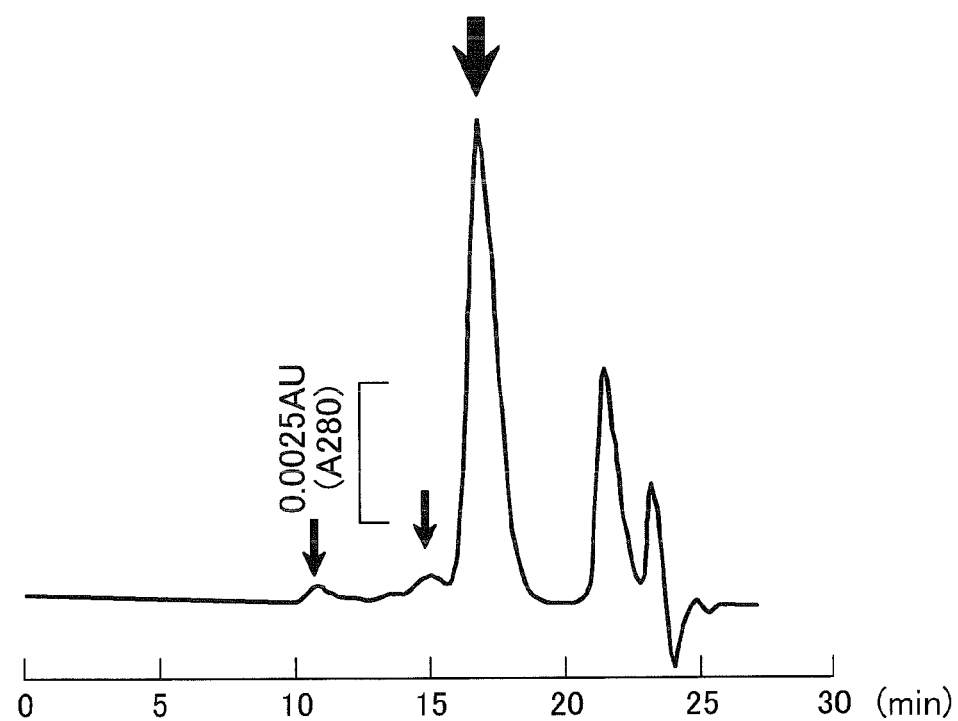

Next, 15 µl of the same mouse monoclonal antibody sample after the heat treatment was subjected to gel filtration chromatography under exactly the same conditions, except that arginine hydrochloride was added to the developing solvent during gel filtration chromatography to give 0.2 M. Thus, as shown in FIG. 1-2, both the kind and amount of the detected peaks drastically increased in comparison to an absence of arginine (FIG. 1-1). Total recovery yield of the peaks of the detected antibody monomer and aggregates was 92.8% of that before heating, which is almost completely consistent with the 92.4% value that was obtained based on the absorbance. The content of the aggregates occupying the entire peaks then was 67.4%. The approximate consistency of the recovery yield of the entire peaks with the quantitative determination according to optical density measurement suggested that the addition of arginine to the developing solvent enables quantitative recovery of the aggregates of the antibody, which could not be correctly detected under conventional conditions, and, as a result, the content of the aggregates in the supernatant can be accurately determined.

To the contrary, the content of the aggregates in the case where arginine was not added to the developing solvent was estimated to be as low as 21.7%. This is a quantitative value erroneously obtained due to insufficient recovery yield of the aggregates from the column.

TABLE 1

Results of analysis of mouse monoclonal antibody after heat treatment

| Analysis method | Content of aggregates | Total yield of monomer and associated form(*) |
|---|---|---|
| Gel filtration chromatography (FIG. 1-1: sodium phosphate alone) | 21.7% | 18.5% |
| Gel filtration chromatography (FIG. 1-2: sodium phosphate + 0.2 M arginine hydrochloride) | 67.4% | 92.8% |
| Optical density method | —(**) | 92.4% |

(*)Recovery yield of the amount of the antibody after the heat treatment to the amount of the antibody before the heat treatment
(**)Antibody monomer and antibody aggregates being indistinguishable From the results described above, when an antibody solution containing aggregates is purified by gel filtration chromatography, the method is efficacious not only for an analysis but also as a method of production of an antibody because purification by gel filtration chromatography can be performed repeatedly without leaving the aggregates on the column.

EXAMPLE 2

10 μl of a solution of 0.70 mg/ml human activin (U.S. Pat. Nos. 6,084,076, and 6,756,482) dissolved in 70 mM sodium acetate (pH 5.0) was subjected to gel filtration chromatography on a Superdex 75HR 10/30 column (manufactured by Amersham Bioscience K.K.) using 0.1 M sodium phosphate and 0.75 M sodium chloride (pH 7.3) as the developing solvent at a flow rate of 0.8 ml/min. Elution performance of the peak was studied using ultraviolet absorption at a wavelength of 280 nm as a marker. As shown in FIG. 2-1, human activin was detected at the same position as salts, and the peak area was calculated to be 200290 from the absorption at a wavelength of 280 nm. There were no peaks detected at an elution position consistent with the molecular weight of human activin (26000 Dalton). The foregoing results suggest that purification by gel filtration chromatography of human activin was not successful, and thus, the aggregate content could not be determined.

Alternatively, 10 μl of the same solution of human activin was subjected to gel filtration chromatography under the same conditions, except that 0.75 M arginine hydrochloride was added in place of 0.75 M sodium chloride in the developing solvent for the aforementioned gel filtration chromatography. Accordingly, as shown in FIG. 2-2, human activin was found as a symmetric peak at an elution position that was consistent with its molecular weight (26000 Da). The peak area was calculated to be 155027 based on the absorption at a wavelength of 280 nm. Furthermore, a peak of the aggregates was found forward of the human activin, with a peak area of 3687. According to the ratio of the peak area, the aggregate content was calculated to be 2.3%. As described above, when using a general buffer as the developing solvent in gel filtration chromatography of human activin, separation of a peak is not possible. However, adding arginine to the developing solvent enabled separation of the human activin peak.

EXAMPLE 3

Figures 1, 3:
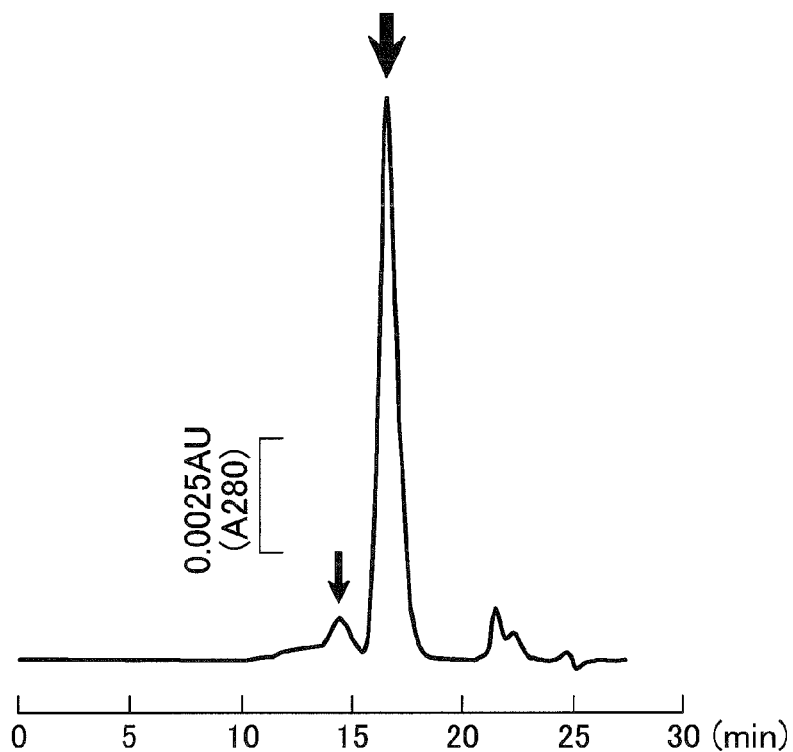
Figures 2, 3:
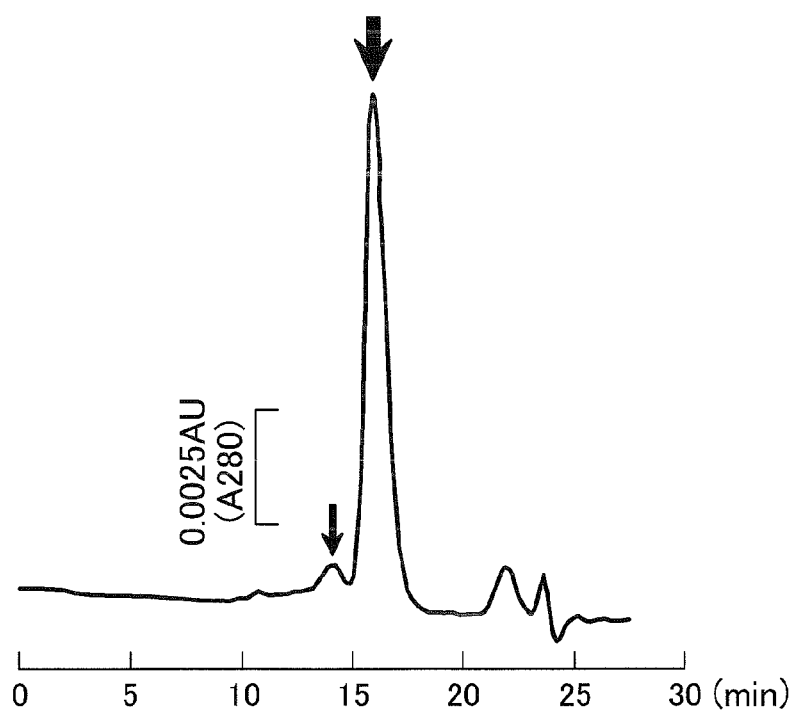

Human interleukin 6 (U.S. Pat. No. 5,610,284) was dissolved to give 2.13 mg/ml in 10 mM sodium citrate and 8.7 mM sodium phosphate (pH 7.0) in a volume of 3.5 μl and was subjected to gel filtration chromatography on a Superdex 75HR 10/30 column (manufactured by Amersham Bioscience K.K.) using 0.1 M sodium phosphate, 0.75 M sodium chloride (pH 7.3) as the developing solvent at a flow rate of 0.8 ml/min. Elution performance of the peak was studied using the ultraviolet absorption at a wavelength of 280 nm as a marker. As shown in FIG. 3-1, the monomer and the aggregates of human interleukin 6 were separated. The monomer was detected as a highly symmetric peak at an elution position that is consistent with the molecular weight (21000 Dalton) of human interleukin 6, the peak area of which was calculated to be 182028 based on the absorption at a wavelength of 280 nm. The peak area of the aggregates eluted forward of the monomer, and was calculated to be 9012. Based on the ratio of the peak area, the aggregate content was calculated to be 4.7%. On the other hand, 3.5 μl of the same solution of human interleukin 6 was subjected to gel filtration chromatography under the same conditions, except that 0.75 M arginine hydrochloride replaced 0.75 M sodium chloride in the developing solvent for the aforementioned gel filtration chromatography.

Accordingly, as shown in FIG. 3-2, human interleukin 6 was found as a symmetric peak at an elution position that is consistent with its molecular weight (21000). The peak area was calculated to be 182226 based on the absorption at a wavelength of 280 nm. Furthermore, the peak area of the aggregates eluted forward of the monomer, and was calculated to be 4779. According to the ratio of the peak area, the composition ratio of the aggregates was calculated to be 2.6%. It was revealed that human interleukin 6 is favorably separated and recovered in peaks of the monomer and the aggregates in gel filtration chromatography, irrespective of whether the salt added to the developing solvent is sodium chloride or arginine hydrochloride. Also in cases where arginine hydrochloride was added, the aggregates were properly separated and recovered. Therefore, that the presence of arginine hydrochloride in the developing solvent does not permit the aggregates to dissociate into the monomer during progress of the analysis, thereby avoiding an unreasonably low aggregate content.

EXAMPLE 4

Figures 1, 4:
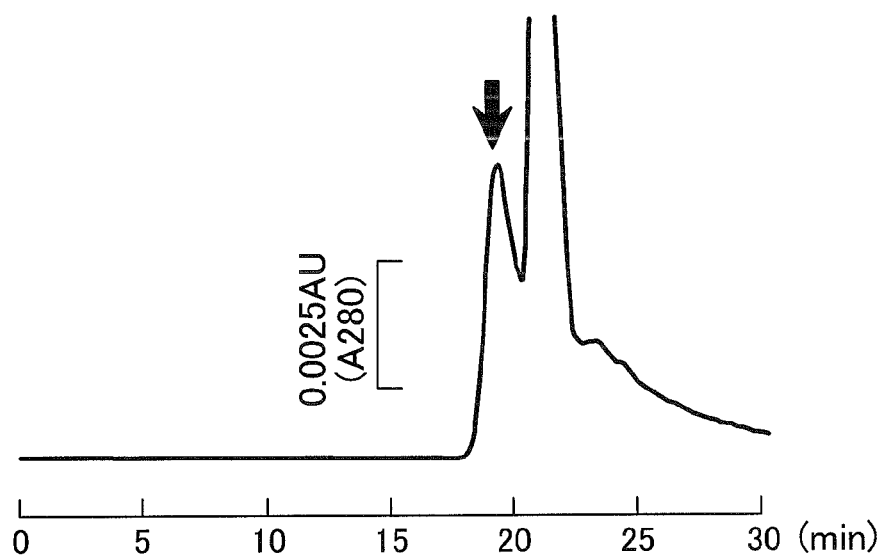
Figures 2, 4:
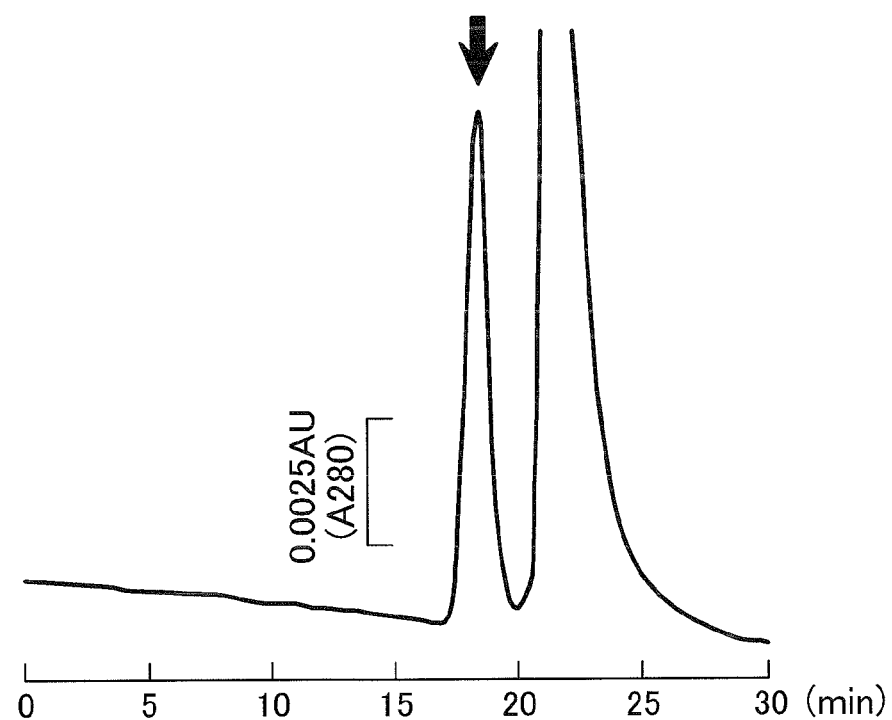

Human fibroblast growth factor (manufactured by Biosource Inc., Catalog No. PHG0026) was dissolved in pure water and adjusted to give a concentration of 0.25 mg/ml. 20 μl of this solution was subjected to gel filtration chromatography on a Superdex 75HR 10/30 column (manufactured by Amersham Bioscience K.K.) using 0.1 M sodium phosphate, 0.2 M sodium chloride (pH 6.8) as the developing solvent at a flow rate of 0.8 ml/min. The elution performance of the peak was studied using ultraviolet absorption at a wavelength of 280 nm as a marker. As shown in FIG. 4-1, peak of the human fibroblast growth factor was found later than the elution position expected from its molecular weight (17000), and the peak area thereof was calculated to be 59281 based on the absorption at a wavelength of 280 nm.

Alternatively, 20 μl of the same human fibroblast growth factor solution was subjected to gel filtration chromatography under the same conditions except that 0.2 M arginine hydrochloride replaced 0.2 M sodium chloride in the developing solvent for the aforementioned gel filtration chromatography. Accordingly, as shown in FIG. 4-2, human fibroblast growth factor eluted at a position slightly forward of that with sodium chloride as described above, and the peak area thereof was calculated to be 154616 based on the absorption at a wavelength of 280 nm. The shifting forward of the elution position of the peak and that the peak area increased 2.6 times through the addition of arginine hydrochloride in place of sodium chloride suggested that unnecessary interaction between the human fibroblast growth factor and the column was attenuated. Additionally, in this instance, any peak of the aggregates was not detected regardless of the presence of arginine; therefore, the aggregate content was not calculated.

EXAMPLE 5

Figures 1, 5:
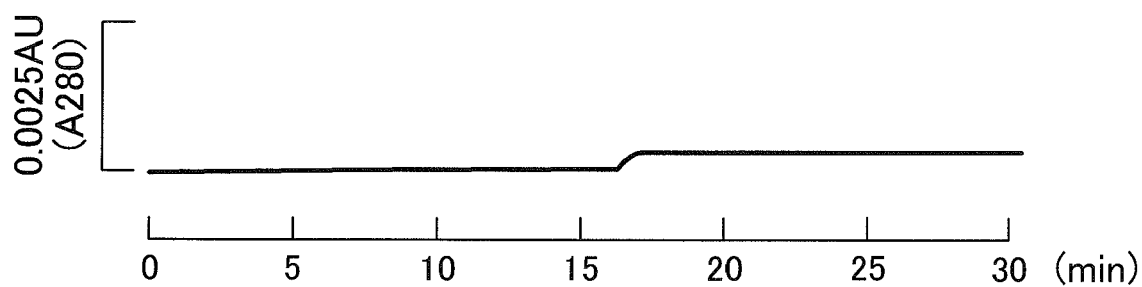
Figures 2, 5:
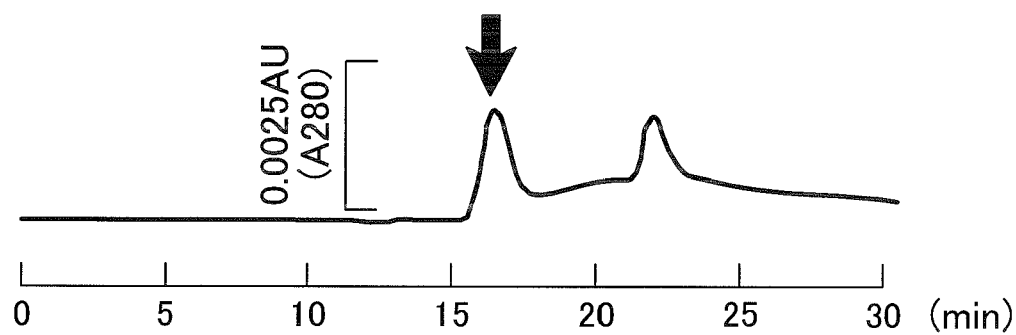

5 μl of 0.96 mg/ml human interferon gamma (manufactured by Biosource Inc., Catalog No. PHC4031) dissolved in 40 mM Tris HCl buffer (pH 7.4) was subjected to gel filtration chromatography on a Superdex 75HR 10/30 column (manufactured by Amersham Bioscience K.K.) using 0.1 M sodium phosphate, 0.4 M sodium chloride (pH 6.8) as the developing solvent at a flow rate of 0.8 ml/min. The elution performance was studied using the ultraviolet absorption at a wavelength of 280 nm as a marker. As shown in FIG. 5-1, no elution peak was detected. Similarly, no peaks were detected when the sodium chloride concentration in the developing solvent was lowered to 0.2 M, nor to 0 M. Furthermore, no peaks were detected when 1 M of the protein denaturating agent urea replaced sodium chloride.

Alternatively, 5 μl of the same human interferon gamma was subjected to gel filtration chromatography under the same conditions, except that 0.4 M arginine hydrochloride replaced the sodium chloride or urea in the developing solvent for the aforementioned gel filtration chromatography. Accordingly, as shown in 5-2, the elution peak was detected, and the peak area was calculated to be 26914 based on the absorption at a wavelength of 280 nm. As described above, gel filtration chromatography of human gamma interferon, the peak of which can be neither separated nor recovered by gel filtration chromatography when a general buffer is used as the developing solvent, was enabled by adding arginine to the developing solvent. Additionally, in this instance, no aggregate peak was detected regardless of the presence or absence of arginine; therefore, the aggregate content was not calculated.

While the invention has been described in detail with reference to exemplary embodiments thereof, it will be apparent to one skilled in the art that various changes can be made, and equivalent employed, without departing from the scope of the invention. Each of the aforementioned documents is incorporated by reference herein in its entirety.

What is claimed is:

1. A method for performing gel filtration chromatography of a solution containing an antibody which is present as an aggregate without dissociating the aggregate into monomers during the chromatography, comprising
    adding 0.05 M to 1.5 M arginine and/or an arginine derivative to a developing solvent utilized during said chromatography during elution.

2. The method according to claim 1, wherein the concentration of the arginine and/or the arginine derivative in the developing solvent is 0.05 to 1.25 M.

3. The method according to claim 1, wherein the concentration of the arginine and/or the arginine derivative in the developing solvent is 0.10 to 0.75 M.

* * * * *